United States Patent
Grubac et al.

(10) Patent No.: US 8,326,392 B2
(45) Date of Patent: Dec. 4, 2012

(54) FOLDABLE SENSOR DEVICE AND METHOD OF USING SAME

(75) Inventors: Vladimir Grubac, Brooklyn Park, MN (US); Peter R. Rosendahl, Minneapolis, MN (US)

(73) Assignee: Nonin Medical, Inc., Plymouth, MN (US)

( * ) Notice: Subject to any disclaimer, the term of this patent is extended or adjusted under 35 U.S.C. 154(b) by 1560 days.

(21) Appl. No.: 11/679,595

(22) Filed: Feb. 27, 2007

(65) Prior Publication Data

US 2008/0208023 A1 Aug. 28, 2008

(51) Int. Cl.
*A61B 5/1455* (2006.01)

(52) U.S. Cl. .......... 600/344; 600/310; 600/323

(58) Field of Classification Search .......... 600/310, 600/323, 344, 324, 326, 340
See application file for complete search history.

(56) References Cited

U.S. PATENT DOCUMENTS

| | | | |
|---|---|---|---|
| 5,209,230 A | | 5/1993 | Swedlow et al. |
| 5,237,994 A | * | 8/1993 | Goldberger .......... 600/323 |
| 5,452,717 A | * | 9/1995 | Branigan et al. .......... 600/323 |
| 6,149,481 A | | 11/2000 | Wang et al. |
| 6,546,267 B1 | | 4/2003 | Sugiura et al. |
| 6,745,061 B1 | | 6/2004 | Hicks et al. |
| 6,763,256 B2 | | 7/2004 | Kimball et al. |
| 2003/0171662 A1 | * | 9/2003 | O'Connor et al. .......... 600/323 |
| 2003/0181799 A1 | * | 9/2003 | Lindekugel et al. .......... 600/344 |
| 2004/0087845 A1 | | 5/2004 | Katarow et al. |
| 2004/0116787 A1 | * | 6/2004 | Schnall .......... 600/310 |
| 2006/0106294 A1 | | 5/2006 | Maser et al. |
| 2007/0032710 A1 | | 2/2007 | Raridan et al. |
| 2007/0078317 A1 | | 4/2007 | Matlock |
| 2007/0123756 A1 | | 5/2007 | Kitajima et al. |
| 2010/0210924 A1 | | 8/2010 | Parthasarathy et al. |

FOREIGN PATENT DOCUMENTS

| | | |
|---|---|---|
| WO | WO-2008106528 A2 | 9/2008 |
| WO | WO-2008106528 A3 | 9/2008 |
| WO | WO-2010096475 A1 | 8/2010 |

OTHER PUBLICATIONS

"International Application Serial No. PCT/US08/55155, International Search Report and Written opinion mailed Aug. 26, 2008", 15 pgs.
"International Application Serial No. PCT/US2008/055155, International Preliminary Examination Report mailed Sep. 11, 2009", 12 pgs.
"International Application Serial No. PCT/US2010/024464, Search Report mailed May 27, 2010", 6 pgs.
"International Application Serial No. PCT/US2010/024464, Written Opinion mailed May 27, 2010", 5 pgs.
"Japanese Application Serial No. 2009-551826", Voluntary Amendment Filed Feb. 25, 2011, 15 pgs.

* cited by examiner

*Primary Examiner* — Eric Winakur
*Assistant Examiner* — Chu Chuan (JJ) Liu
(74) *Attorney, Agent, or Firm* — Schwegman Lundberg & Woessner, P.A.

(57) ABSTRACT

A physiologic sensor device configured to be placed on an appendage. The sensor device includes a foldable portion designed to be deformed around the tip of the appendage. In some embodiments the foldable portion is a soft compressible material. In other embodiments a stabilization component is provided to isolate sensing elements from external forces. Some embodiments also include a deformable frame that folds in response to a bending force as the sensing device is placed on the appendage. The deformable frame holds the sensor device in place until another bending force is applied. In other embodiments the frame and/or sensor elements are removable and disposable relative to other components of the sensor device.

35 Claims, 6 Drawing Sheets

FIG. 1C
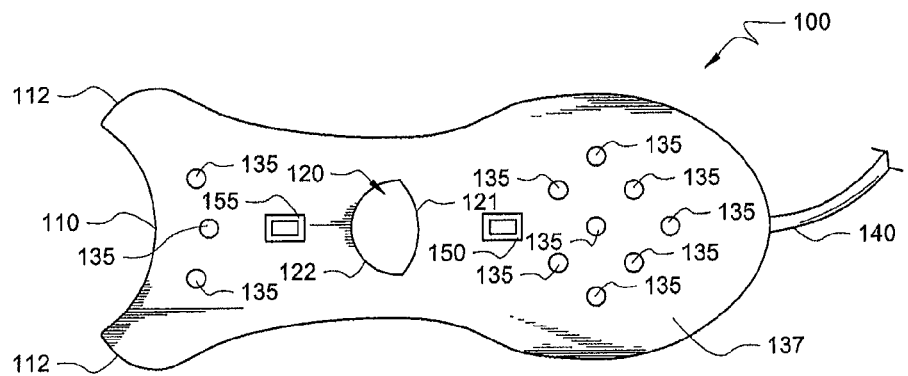
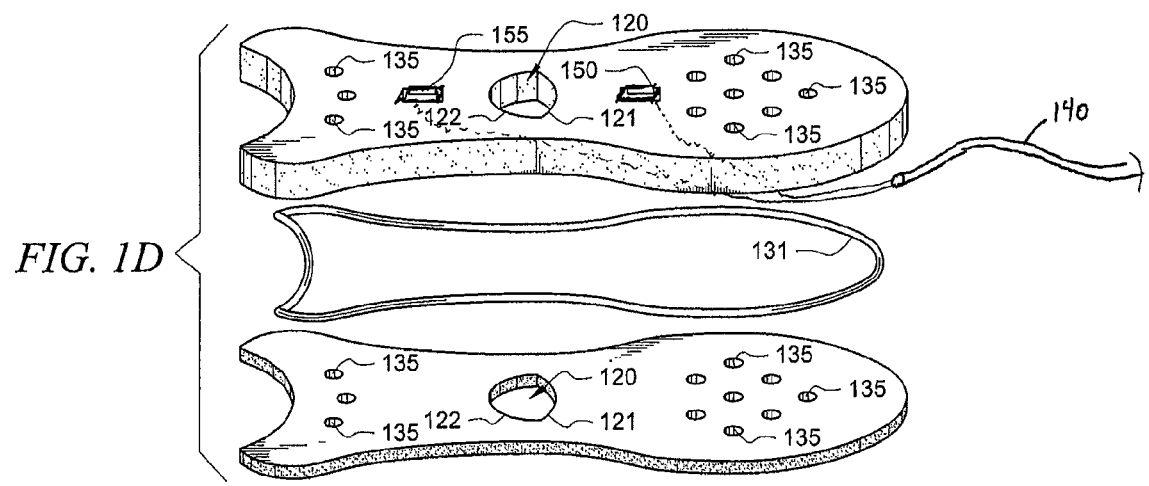
FIG. 1D

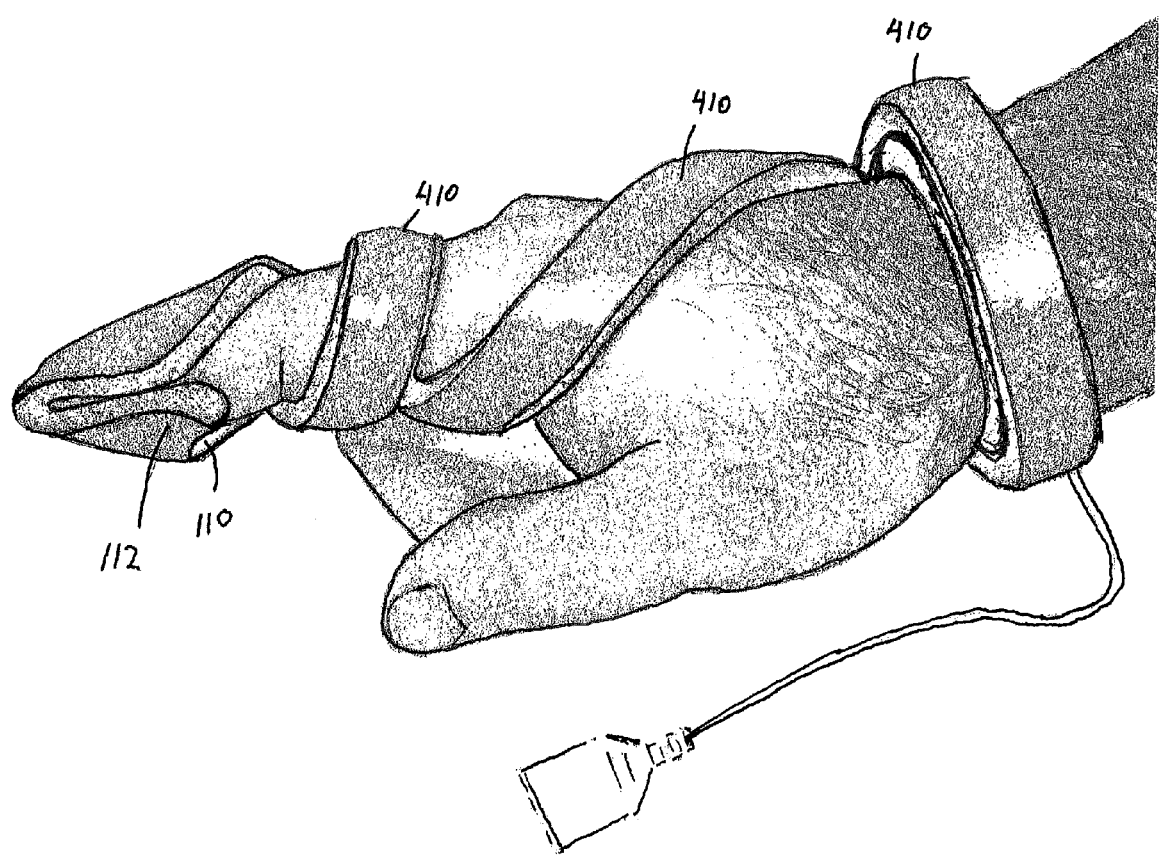
Fg 4B

FOLDABLE SENSOR DEVICE AND METHOD OF USING SAME

TECHNICAL FIELD

The present disclosure is directed to physiologic sensors. More specifically, the present disclosure is directed to a sensor device that can be folded to conform about an appendage by a patient or care provider.

BACKGROUND OF THE INVENTION

Pulse oximetry involves the non-invasive monitoring of oxygen saturation level in blood-profused tissue indicative of certain vascular conditions. Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photo-electrically senses the absorption of light in such tissue. The amount of light absorbed is then used to calculate the amount of blood constituent being measured. Oxygen saturation may be calculated using some form of the classical absorption equation know as Beer's law. The light passed through the tissue is typically selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two or more different wavelengths, in accordance with known techniques for measuring blood oxygen saturation.

Known pulse oximetry sensors include an optical element which uses a pair of light emitting diodes (LEDs) to direct light through blood-perfused tissue, with a photodetector receiving light which has not been absorbed by the tissue. Accurate pulse oximeter measurements require relatively stable positioning of the sensor on an appendage, as well as proper alignment between the light source and light detector.

Accurate measurement of oxygen saturation levels are predicated upon optical sensing in the presence of arterial blood flow. A finger provides a convenient access to a body part through which light will readily pass. Other body appendages may also be used, e.g., toes and ears. Local vascular flow in a finger is dependent on several factors which affect the supply of blood. Blood flow may be affected by centrally mediated vasoconstriction, which must be alleviated by managing the perceived central causes. Peripheral constriction via external compression, however, can be induced by local causes. One such cause of local vasocompression is the pressure exerted by the sensor on the finger.

Many currently available pulse oximetry finger sensors have a hard shell which is maintained upon the finger tip by spring action. Since excess pressure on the finger can distort or eliminate the pulsation in the blood supply to the finger, these springs are intentionally relatively weak. The result of this compromise is that the spring-held sensors readily fall off the finger. Resilient polymer sensors are also known, such as disclosed in US Patent Publication No. 20060106294, incorporated by reference herein and assigned to Nonin Medical, Inc., the assignee of the present application. One limitation of these types of sensors has been user discomfort, particularly during extended periods of sensor use.

Many known non-disposable oximeter sensors are relatively bulky and exhibit a relatively high inertia of the housing relative to the finger. This results in a susceptibility to disturbance between the sensor and the finger surface as the patient's hand is moved. This relative motion manifests itself as motion artifacts in the detected signal. Motion artifacts, for example caused by tension on the lead wire, are especially problematic for pulse oximeter systems.

Pulse oximeter sensors are used in a number of applications where they are susceptible to being disturbed or displaced entirely from the appendage. Many oximeter finger sensors locate the lead wire from the sensor over a central portion of a patient's finger. When the patient flexes or curls his finger, the lead wire is often pulled against the sensor causing the light elements to be displaced.

BRIEF SUMMARY OF THE INVENTION

The present invention is directed to a medical sensor device configured to be placed on an appendage of, for example, a patient. The sensor device is adapted to conform to an appendage upon application of an external folding force. The sensor device includes a portion designed to fold around the appendage and position optical sensor elements on or near a tissue surface of the appendage. In some embodiments the foldable portion includes a soft compressible material. In some embodiments a stabilization component is provided. The stabilization component helps keep the sensor device in place when inadvertently disturbed, for example, by an external force. Some embodiments also include a flexible stiffening portion or frame that is folded over as the sensor device is folded on the appendage. The flexible stiffening portion or frame tends to maintain the sensor device comfortably in place until it is repositioned or removed.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1C is a bottom view of the sensor device;

FIG. 1D is a partially exploded top view of the sensor device;

FIG. 4B illustrates the pulse oximeter on a finger according to one embodiment

DETAILED DESCRIPTION OF THE INVENTION

Figure 1A:
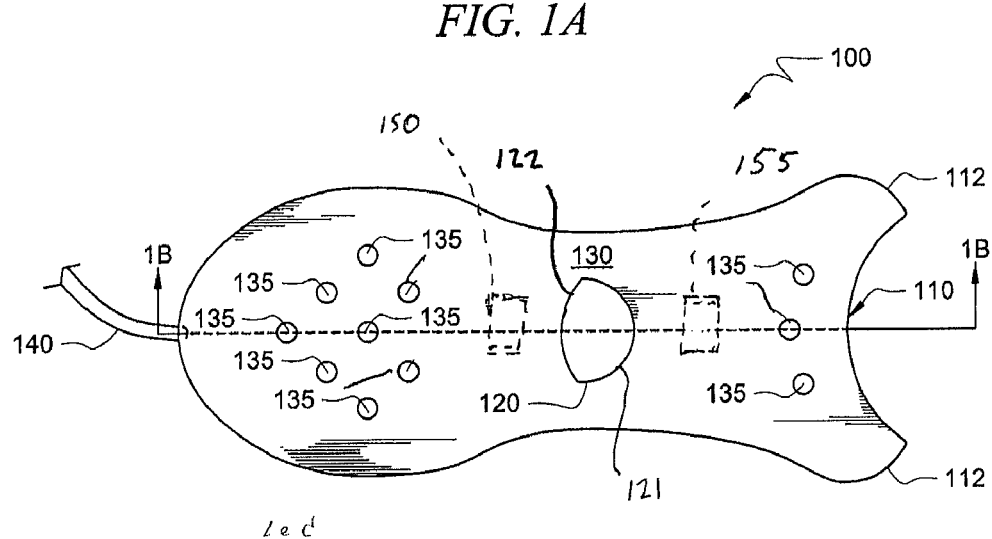
FIG. 1A is a top view of a sensor device according to one illustrative embodiment.
Figure 1B:
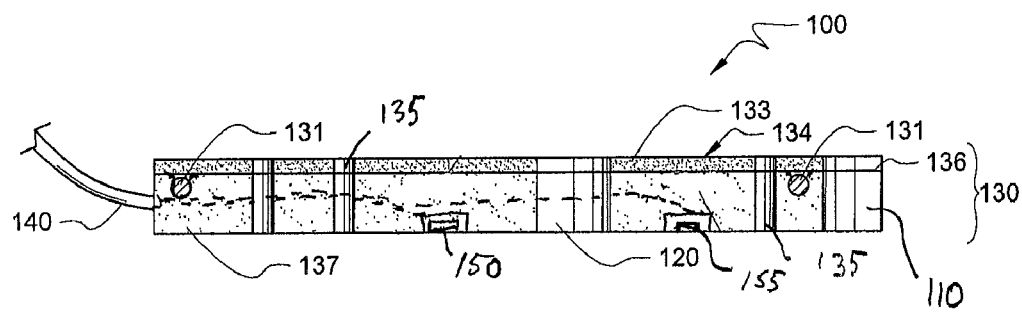
FIG. 1B is a cut away view of the sensor device.

FIG. 1A is a top view of a sensor according to one illustrative embodiment. FIG. 1B is a side view of the sensor cut taken along line B-B of FIG. 1A. FIG. 1C is a bottom view of the sensor. FIG. 1D is a partially exploded top view of the sensor. For purposes of this discussion FIGS. 1A, 1B, 1C and 1D will be discussed together. In one embodiment, sensor 100 is a pulse oximeter sensor utilized within a pulse oximetry system. For the purposes of explanation only, sensor 100 is configured for the measurement of oxygen saturation through known oximetric transmittance techniques. As one skilled in the art can readily appreciate, the present invention is easily adaptable to accommodate a number of different physiological monitoring applications and configurations, including but not limited to, other optical sensors, reflective sensor, etc.

Sensor 100 includes foldable portion (or member or substrate) 130, optical sensor elements 150, 155 and a communications link including lead 140 which couples sensor 100, for example, to a monitor. A pulse oximeter system is configured to measure blood oxygenation levels by fitting sensor 100 over at least a portion of a phalange (such as a finger or toe) of the body. Sensor 100 could also be placed on other body parts, e.g., ears and nose.

Foldable portion 130 in some embodiments is made from two different materials. These two materials are designated as a top material 133 and bottom material 137. However, other arrangements can be envisioned. Top material 133 is disposed on a top portion of foldable portion 130. Conversely, bottom material 137 is disposed on a bottom portion of foldable portion 130. When folded around an appendage the top material 133 forms the outside of the pulse oximeter, and bottom material 137 forms the inside of the sensor in direct contact with the finger surface.

Foldable materials for use in foldable portion 130 include, but are not limited to, foams, plastics, fabrics, leathers, papers and other materials in cellular form. In some embodiments materials 133 and 137 have different material properties that allow sensor 100 to be both resilient and provide cushioning. In one embodiment material 137 is a readily compressible polyethylene foam. However, other cushioning, compressible or foam materials can be used for bottom material 137. Top material 133 is, in one embodiment, also a polyethylene foam. However, unlike bottom material 137, the polyethylene foam of top material 133 is significantly more dense and less compressible than bottom material 137. Further, in some embodiments, top material 133 can include a protective layer or coating on an outside portion 134 that both protects the underlying material(s). Again, other materials can be used for top material 133. In other embodiments the top and bottom materials can be the same material with no noticeable differentiation between the two materials.

Disposed at an interface 136 between materials 133 and 137 is a deformable frame 131. However, in other embodiments frame 131 can be located elsewhere, such as on the outside of either material 133 or 137. Frame 131 is in one embodiment a rigid material (as compared to materials 133 or 137) that is readily folded over and deformed from a flat form into a curved shape. Once bent into a shape, such as during application of sensor 100 to a finger, frame 131 tends to substantially maintain its shape until such time as an additional bending force is applied. In one embodiment, frame 131 is initially generally flat so that sensor 100 can be shipped flat and then deformed into positioned over the finger prior to use. Preferably, frame 131 and materials 133, 137 together combine to minimize disturbances of optical sensor elements 150, 155 in response to external forces. As a result, a reduction in motion artifacts is provided along with improved user comfort. In one embodiment frame 131 is a metal wire that is disposed near an outer perimeter of sensor 100. However, frame 131 can utilize other materials or be of different cross-sectional shape. For example, frame 131 may include a metal stamping or die-cut part. Frame 131 may be a disposable component within a sensor device kit. Frame 131 is preferably formed from a malleable material.

Disposed within foldable portion 130 is the pair of optical sensor elements 150 and 155. In one embodiment, element 150 includes a pair of light emitting diodes (LED) and element 155 is a photodiode. Other illumination methods can be used. In one embodiment LEDs 150 include one LED emitting red light having a wavelength of 660 nm, and a second LED emitting infrared light having a wavelength of 910 nm. However, other wavelengths that produce red and infrared light can be used. In alternative embodiments of sensor 100, alternative or additional LEDs can be used.

Photodiode 155 is arranged to receive light signals from LEDs 150 during an optical sensing process. In one embodiment, photodiode 155 receives both red and infrared light that has passed from LEDs 150 through the finger. Photodiode 155 provides a signal coupled through lead 140 to, for example, a remote monitor for further processing and interpretation. In alternative embodiments, LEDs 150 can be collocated next to or near photodiode 155. For example, LEDs 150 and photodiode 155 may be provided adjacent each other to facilitate a reflectance-type optical sensing process instead of the above described transmittance-type sensing.

In some embodiments sensor elements 150 and 155 can be provided on a flexible sheet which is initially separate from foldable portion 130. When such elements are disposed on a separate sheet, foldable portion 130 may have a slit or other opening to allow the insertion of sensor elements 150, 155. Such an arrangement allows for the reuse of optical sensor elements 150, 155. Similarly, in some embodiments frame 131 can be provided as a disposable component which is inserted or otherwise engaged with foldable portion 130 during use and subsequently removed and disposed. In yet another embodiment, frame 131, foldable portion 130 and sensor elements 150, 155 may be separately provided and combined prior to use, with one or all being disposable.

In some embodiments foldable portion 130 also includes a finger hole 120 used to assist in proper positioning of sensor 100 upon a finger. More particularly, finger hole 120 can assist in proper alignment of sensor elements 150, 155 upon the finger. Finger hole 120 is in one embodiment an aperture through foldable portion 130. Finger hole 120 is defined in some embodiments by two separate radii 121 and 122. These radii generally correspond to the radii of a bottom and top radii found on a finger. However, in some embodiments, finger hole 120 can be replaced with an indent or bump within foldable portion 130. This indent or bump can be present in bottom material 137 or top material 133 and felt by a patient upon application of sensor device 100 on a finger.

Foldable portion 130 in some embodiments includes a number of holes or apertures 135. Holes 135 are arranged in foldable portion 130 to allow for air flow circulation across finger surfaces covered by sensor 100. Depending on the selection of materials of foldable portion 130, in some embodiments apertures 135 are not needed as the materials of foldable portion 130 are selected to provide sufficient breathability to covered finger surfaces.

In some embodiments foldable portion 130 of sensor 100 includes a curved portion 110. Curved portion 110 is shaped such that when sensor 100 is folded over a finger the curved portion is positioned, in one embodiment, between the first and second knuckle of the finger which allows for natural movement of the finger, yet resists rotation of sensor 100 upon the finger. However, this feature need not be present in all embodiments. Additionally, depending on the size of the finger, the location of curved portion 110 relative to the finger knuckles can change.

Figure 2:
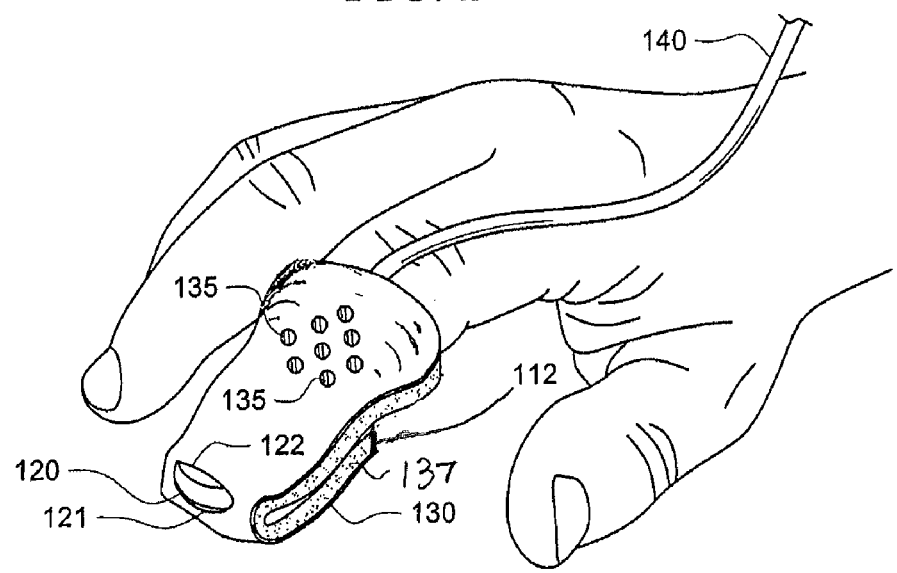
FIG. 2 is a diagrammatic view of the sensor device in place over a finger.

In some embodiments foldable portion 130 includes deformable "winglet" ends 112 near, for example, curved portion 110 which can be deformed to provide a more secure attachment of sensor 100 to the finger or other appendage. Winglet ends 112, in one embodiment, are embodied as a widened portion of sensor 100 as compared to a width proximate to finger hole 120. As shown in FIGS. 2 and 4B, winglet ends 112 can be configured in one embodiment to allow sensor 100 to be folded over upon a finger tip with portions of soft foam material 137 engaging each other without respective portions of harder cover material 133 engaging each other.

Lead 140 is in one embodiment a series of wires that are connected to a remote monitoring device. The remote monitoring device can be in the same room as the patient or can be located elsewhere. However, in some embodiments a wireless communication component may be provided upon or within sensor 100 to communicate to a remote monitor via one of many known medical device wireless protocols (e.g., BLUETOOTH).

FIG. 2 is a diagrammatic view of sensor 100 upon a finger 200. In this figure, sensor 100 has been folded over the finger. Curved portion 110 is illustrated interfacing with the bottom of the finger between the first and second knuckle. Lead 140 is shown following along the hand and away from the body. The tip of the finger can be observed protruding slightly from aperture 120. Frame 131 is holding sensor 100 in the desired position.

For purposes of completeness a brief description of a process of using sensor 100 will be provided. In one embodiment, sensor 100 is provided in a generally flat form. A finger tip then engages the flattened sensor 100 at finger hole 120. Once the finger tip has been aligned with the finger hole 120 (assisted, for example, by dual radii 121, 122) the user or caregiver then folds sensor 100 over and around the finger. During this folding process frame 131 is deformed around the finger. The bending process deforms frame 131 and foldable portion 130 and allows sensor 100 to remain comfortably in place upon the finger.

Figure 3A:
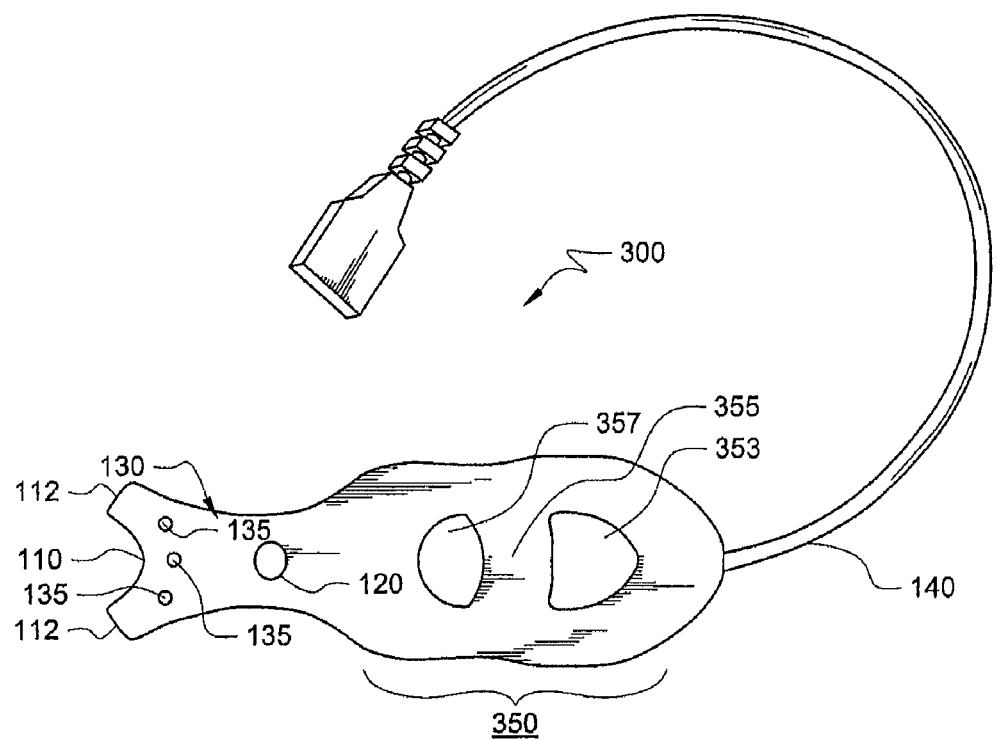
FIG. 3A is a is a diagrammatic view of a pulse oximeter according to an alternative embodiment.

FIG. 3A is a diagrammatic view of a pulse oximeter 300 according to an alternative embodiment of the present invention. For purposes of simplicity, reference numbers in FIG. 3A that correspond to reference numbers in FIGS. 1A-1D refer to the same or similar features.

Sensor 300 includes curved portion 110, foldable portion 130, communications lead 140, and stabilization component 350. In such an embodiment sensor 300 is configured to provide additional stabilization to resist disturbance of optical sensor elements 150, 155 from external forces during use. For example, an external force may be transferred to sensor 300 through lead 140, e.g., by pulling on lead 140. Such contact with lead 140 may cause sensor elements 150, 155 to be displaced or entirely removed from the finger.

Stabilization component 350 helps prevent the inadvertent movement of sensors 150 and 155 in response to an external force applied to sensor 300. Stabilization component 350 includes first aperture 353, second aperture 357 and bridge portion 355. In some embodiments, frame 131 is present as well within stabilization component 350. Apertures 353, 357 are sized such that a finger can pass through during placement. When placing sensor 300 on a patient, a finger is inserted from the bottom of sensor 300 through aperture 353, over support bridge 355 and then through aperture 357. Once the finger is placed through apertures 353 and 357, the fingertip is then directed into finger hole 120. Foldable portion 130 is then folded over the finger, as described above, such that a desired application is provided.

Figure 3B:
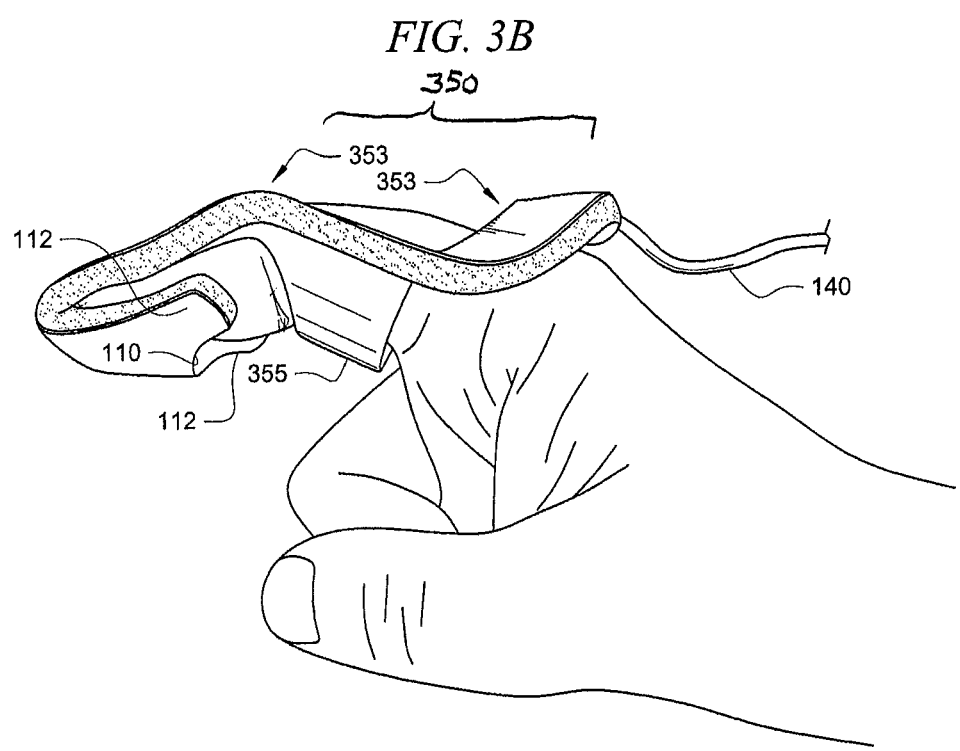
FIG. 3B illustrates the pulse oximeter on a finger according to one embodiment.

FIG. 3B illustrates sensor 300 on a finger according to one embodiment. In this configuration stabilization component 350 engages upper and lower finger surfaces away from optical sensor elements 150, 155 to help stabilize sensor 300 upon the finger. In one embodiment, forces applied to communications link 140 are transferred through the stabilization component 350 to the finger. For a small external force, the stabilization component 350 transfers the force to finger surfaces engaged by the stabilization component 350 without causing disturbance to sensor elements 150, 155. For many external forces applied to sensor 300, the stabilization component 350 isolates the optical sensor elements 150, 155 from displacement, leading to a reduction in motion artifacts.

Figure 4A:
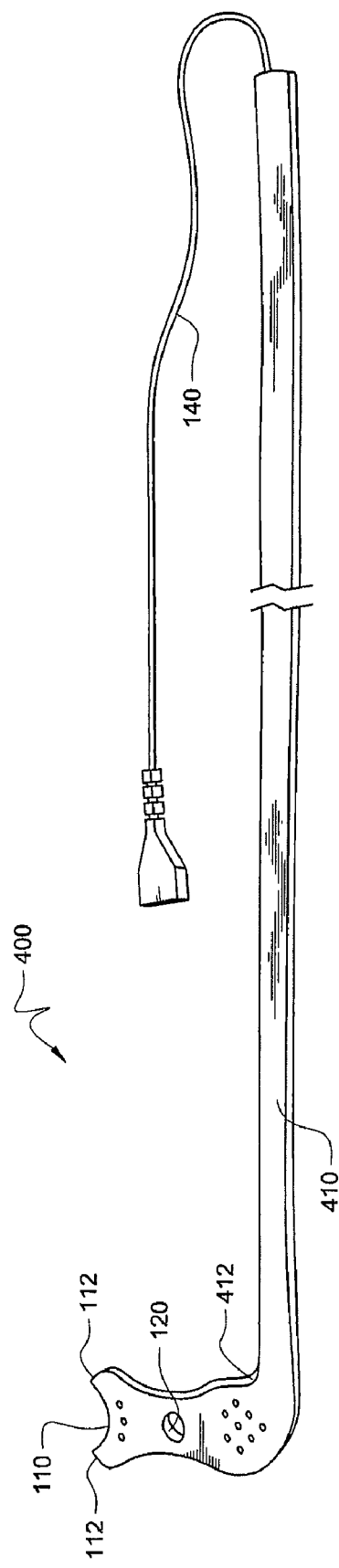
FIG. 4A is a is a diagrammatic view of a pulse oximeter according to an alternative embodiment.

FIGS. 4A and 4B illustrate yet another embodiment of a sensor 400 in accordance with the present invention. The components of pulse oximeter 400 are similar to those of pulse oximeter 100 in FIGS. 1A-1D. Pulse oximeter 400 is in one embodiment designed to be used in sleep studies. In sleep studies it is often desirable to measure the patient's pulse rate and oxygenation levels while they sleep. Further, sensor devices should be non-invasive and as comfortable as possible so as not to disrupt the participant's sleep. However, in most sleep studies it is extremely difficult to maintain a sensor device in place through all sleep cycles. Tossing and turning of the study participant during sleep often results in the sensor device being pulled off or displaced.

Sensor 400 is provided with a wrapping tail 410 as a stabilizing component to reduce the likelihood that the sleep study participant will dislodge sensor 400 while sleeping. In one embodiment, wrapping tail 410 extends from a front portion 412 of sensor 400. Wrapping tail 410 preferably has a length that is sufficient to permit tail 410 to be wrapped a number of times around the finger and wrist of the participant, as illustrated by FIG. 4B. By so wrapping tail 410 around the finger and wrist, sensor 400 provides a stable platform for sensor elements 150, 155 which is resistant to forces transferred through lead 140. In one application, as shown in FIG. 4B, at tail 410 is wrapped a full turn around the finger, preferably between the $2^{nd}$ and $3^{rd}$ knuckles prior to being wrapped around the wrist.

In some embodiments frame 131 is provided within wrapping tail 410 to further assist in maintaining sensor 400 in place. In other embodiments, an adhesive or hook-and-loop type fastener upon tail 410 may be utilized to secured sensor 400 in place. Tail 410 may be a different material from foldable portion 130. For example, tail 410 may be a flexible fabric strap. While the embodiment of FIG. 4 has been described in relation to a sleep study participant, it should be appreciated that sensor 400 may have a variety of other uses.

As shown in FIG. 4B, a portion of the malleable frame 131 is bent along a longitudinal axis of the appendage and another portion of the malleable frame 131 is bent along an axis perpendicular to the longitudinal axis.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A sensor device comprising:
    a foldable member carrying one or more sensor elements;
    a communications link configured to transmit data from said one or more sensor elements, the communications link including a lead coupled to a sensor element;
    a frame engaging said foldable member, the frame including a material that is rigid relative to the foldable member, together said frame and foldable member adapted to be deformed from an initial shape into a customized form providing said one or more sensor elements in a desired orientation relative to a tissue field, with said frame maintaining said foldable member in said customized form; and
    a stabilization component between a lead of said communications link and said one or more sensors elements wherein the stabilization component comprises a first aperture through said foldable member and disposed between said one or more sensor elements and said lead.

2. The sensor device of claim 1 further comprising:
    a flexible cover material connected to the foldable member, said flexible cover material covering a skin surface engaging material.

3. The sensor device of claim 1 wherein the stabilization component further comprises:
    a second aperture through said foldable member and disposed between said first aperture and said one ore more sensor elements; and
    a bridge disposed between said first aperture and second aperture.

4. The sensor device of claim 1 wherein the stabilizing component comprises:
    an elongated tail.

5. The sensor device of claim 4 wherein the tail is configured to wrap around a finger and forearm of a user.

6. The sensor device of claim 1 wherein said one or more sensor elements further comprises:
    a light source; and
    a light detector configured to receive light from said light source through said tissue field.

7. The sensor device of claim 1 wherein the foldable member is removable from said one or more sensor elements.

8. The sensor device of claim 1 wherein said communications link is a wired link to remote site.

9. The sensor device of claim 1 wherein said communications link is a wireless link.

10. The sensor device of claim 1 wherein said foldable member further comprises:
    a first material disposed on a bottom portion of the device; and
    a second material disposed on a top portion of the device.

11. The sensor device of claim 10 wherein the first material is a compressible material.

12. The sensor device of claim 11 wherein the first material is a polyurethane foam.

13. The sensor device of claim 10 wherein the second material is denser than the first material.

14. The sensor device of claim 10 wherein said frame is disposed between the first material and second material.

15. The sensor device of claim 14 wherein said frame is separable and disposable from said foldable component.

16. The sensor device of claim 1 wherein said frame is of malleable material.

17. The sensor device of claim 1 wherein the foldable member has a plurality of apertures arranged to provide air circulation to said tissue field covered by said foldable component.

18. The sensor device of claim 1 further comprising:
    an alignment aperture adapted to be engaged by an appendage tip prior to folding of said foldable member.

19. The sensor device of claim 1 wherein the aperture has a first radius and a second radius, the first radius and the second radius corresponding to radii of said appendage tip.

20. The sensor device of claim 1 wherein the foldable member further comprises:
    a curved portion configured to interface with a bottom portion of an appendage and to allow movement of the appendage when the device is folded.

21. The sensor device of claim 20 wherein the curved portion defines portions of a pair of winglets configured to fold around sides of the appendage.

22. The sensor device of claim 1 wherein a rear section of the foldable member further comprises a stabilization component.

23. The sensor device of claim 22 wherein the stabilization component comprises a first aperture, wherein an appendage is placed through the first aperture prior to folding the device.

24. The sensor device of claim 23 wherein the stabilization component further comprises:
    a second aperture proximate to the first aperture;
    a bridge disposed between the first and second aperture; and
    wherein the appendage is inserted through the second aperture over the bridge and through the first aperture.

25. The sensor device of claim 22 wherein the stabilization component comprises a wrapping tail, the wrapping tail having a length sufficient to wrap around a forearm.

26. A method of attaching a foldable sensor device to an appendage comprising:
    bending a deformable sensor device over an appendage portion so as to position optical sensor elements on either side of the appendage;
    biasing said sensor device in a bent position so as to retain said appendage portion within said sensor device;

wherein said biasing is performed by a rigid deformable frame engaging foldable material in contact with said appendage; and isolating said optical sensor elements with a stabilization component, said stabilization component transferring an external force to the appendage away from the optical sensor elements, wherein said isolating comprises inserting the appendage through a first aperture in the sensor device.

27. The method of claim 26 further comprising:

placing a tip portion of the appendage into an alignment aperture of said sensor device.

28. The method of claim 26 further comprising:

inserting the appendage through a second aperture in the sensor device; and placing the appendage over a bridge located between the first and second apertures.

29. The method of claim 26 wherein said isolating comprises:

wrapping a tail portion of the sensor device around the appendage.

30. The method of claim 29 wherein wrapping the portion of the sensor device, further comprises:

wrapping the portion around a forearm of a patient.

31. The method of claim 26 wherein the frame is initially provided in a flat form prior to being folded before use.

32. A method of adapting an oximeter sensor to an appendage comprising:

bending a deformable sensor device over an appendage into a customized form so as conform portions of said sensor device to said appendage and position elements of a light sensor at a tissue field of the appendage;

maintaining said sensor device in said customized form with a biasing element so as to retain said sensor device upon said appendage and said light sensor elements at the tissue field;

wherein said biasing element is a rigid deformable frame; and isolating said optical sensor elements with a stabilization component, said stabilization component transferring an external force to the appendage away from the optical sensor elements, wherein said isolating comprises inserting the appendage through a first aperture in the sensor device.

33. The method of claim 32 further comprising:

inserting the appendage through a second aperture in the sensor device; and placing the appendage over a bridge located between the first and second apertures.

34. The method of claim 32 wherein said isolating comprises:

wrapping a tail portion of the sensor device around the appendage.

35. The method of claim 32 wherein said frame is enclosed within at least a portion of the sensor device.

* * * * *